(12) United States Patent
Wess

(10) Patent No.: US 6,216,294 B1
(45) Date of Patent: Apr. 17, 2001

(54) DEVICE FOR POSITIONING A PATIENT

(75) Inventor: Othmar Wess, Lengwil-Oberhofen (DE)

(73) Assignee: Storz Medical AG (CH)

( * ) Notice: Subject to any disclaimer, the term of this patent is extended or adjusted under 35 U.S.C. 154(b) by 0 days.

(21) Appl. No.: 09/045,023

(22) Filed: Mar. 20, 1998

Related U.S. Application Data

(63) Continuation of application No. PCT/DE96/01793, filed on Sep. 20, 1996.

Foreign Application Priority Data

Sep. 20, 1995 (DE) .............................. 195 34 956

(51) Int. Cl.$^7$ .................................................. A47B 7/02
(52) U.S. Cl. .................... 5/615; 5/710; 5/713; 5/715; 600/415
(58) Field of Search ................. 5/601, 710, 713, 5/715, 672, 674, 615; 600/415, 425, 427; 378/204, 205

References Cited

U.S. PATENT DOCUMENTS

| 4,171,483 | 10/1979 | Finkenzeller et al. ............... 250/321 |
| 4,346,298 | 8/1982 | Dixit ........................................ 5/441 |
| 4,803,744 | * 2/1989 | Peck et al. ............................... 5/713 |
| 4,873,710 | 10/1989 | Lotman ................................. 378/177 |
| 5,016,268 | * 5/1991 | Lotman ............................. 378/209 X |
| 5,083,550 | * 1/1992 | Krauss et al. ................... 600/427 X |
| 5,287,577 | 2/1994 | Bremer et al. ........................... 5/644 |
| 5,485,839 | * 1/1996 | Aida et al. ........................... 600/427 |

FOREIGN PATENT DOCUMENTS

| 38 28 087 | 2/1990 | (DE) . |
| 0 081 639 | 6/1983 | (EP) . |
| 0365981 | 5/1990 | (EP) . |
| 0369177 | 5/1990 | (EP) . |
| 28375 | * 12/1911 | (GB) ....................................... 5/630 |

OTHER PUBLICATIONS

Storz Medical, "The Modulith SLX–AX", p. 6 (Date Unknown).*

* cited by examiner

Primary Examiner—Terry Lee Melius
Assistant Examiner—James M Hewitt
(74) Attorney, Agent, or Firm—St. Onge Steward Johnston & Reens LLC

(57) ABSTRACT

A device for positioning patients for diagnostic and therapeutic uses having, in particular a horizontally disposed bearer element for the patient (i.e., such as a table). In addition, at least one inflatable or pump-up-able cushion is provided with which the position of the patient, or specific regions of the patient's body, can be altered.

16 Claims, 2 Drawing Sheets

DEVICE FOR POSITIONING A PATIENT

CROSS-REFERENCE TO RELATED APPLICATIONS

This application is a continuation of PCT Application No. PCT/DE96/01793 filed on Sep. 20, 1996.

BACKGROUND AND SUMMARY OF THE INVENTION

The present invention relates to a device for positioning patients for diagnostic or therapeutic purposes having in particular, a horizontally disposed bearer element for the patient, such as a table.

In the course of various examination and treatment procedures, it is frequently necessary to raise or lower certain parts of the body of a patient who is lying on a bed or on a treatment table, in order for example, to obtain access to specific parts of the body or to control blood circulation or movement, via for example, an X-ray contrast agent.

German patent document DE 38 28 087 C2 discloses a generic patient positioning device of this type that has a horizontal hospital bed or a table in which stretching devices can move foils from one position to another position, in which they "surround" the patient. In particular, the foils permit individual adjustable suspension of the patient, and vacuum chambers are provided to stabilize the foils in an evacuated state.

In urological examinations, the patient is frequently moved from a horizontal position into a head-down position, thereby shifting the position of the kidneys, i.e., in the direction of the head. This extends the patient's ureter in such a manner that it is easier to introduce a urethroscope into the patient's ureter. This type of tilting the patient into a head-down position is called "Trendelenburg tilting".

Also in urology, for instance in percutaneous kidney surgery, the middle section of the prone patient is raised in order to gain better access to the site of surgery. Presently, this type of positioning is carried out via suited cushions (complicated mechanical devices located in the surgical table), which permit the separate raising or lowering of specific segments of the surgical table. Another type of positioning is via mechanical tilting of the whole patient table.

The latter mentioned Trendelenburg tilting of the whole patient table is mechanically complicated, thus making the tables very expensive. Moreover, because the table is tilted, the patient may slip, which must be prevented by means of special safety measures, such as shoulder supports.

Treatment tables of this type usually possess no "floating table function" which permits quick positioning of the table, during for example, X-ray examinations. For example, a lithotrity device with a patient table with a floating table function is described in European patent document EP 0 365 981 B1.

The object of the present invention is to provide a device which permits the positioning of a patient in a simple and comfortable manner for specific examination or surgical procedures without, for example, having to forfeit the floating table functions.

This and other objects and advantages are achieved by the positioning apparatus according to the present invention, in which, at least one inflatable cushion or a cushion capable of being filled with a fluid is provided to permit changing the position of the patient or certain parts of the patient's body. In addition, multiple cushions can be employed in parallel or individually with the patient in such a manner that different parts of the body can be positioned simultaneously or individually.

The cushion(s) can be disposed on the (existing) lying surface of the bearer element or the table. Furthermore, the cushion(s) can themselves form the lying surface, or the bearer surface, in such a manner that other devices (for example, ultrasonic diagnostic or therapy units, Xray image amplifiers, etc.) can be disposed on the side of the cushions on which the patient is not lying.

As described in German patent document DE 38 28 087 C2, the bearer element is provided with a frame to which a bearer foil is attached or stretched in a manner that is known, per se. The cushion(s) can be integrated in the bearer foil. The function of the cushions cannot be compared with the known evacuable chambers as known in this printed publication. The cushions are neither intended for changing the position of the patient nor disposed in the region through which the ultrasonic therapy waves are to be applied (cf. col. 3, 11 25–27 of German patent document DE 38 28 087 C2).

In addition, the device according to the invention has the advantage that existing tables (which due to their design do not possess Trendelenburg tilting) can be retrofitted for this type of patient positioning with this device. This includes, for example, lithotrity devices, which are suited for urological examinations but do not possess a mechanical means of tilting the whole table top in a head-down position. Using at least one preferably "wedge-shaped" cushion or multiple cushions (which can be varyingly inflated, disposed side by side in the longitudinal direction of the table), a head-down position of the patient can be obtained without mechanically tilting the whole table.

As previously explained, one preferred embodiment of the invention requires that an inflatable cushion be placed on an existing patient bed in the region where the patient's body is to be raised. The cushion is shaped according to the special anatomical requirements, and can be exchanged and replaced by cushions of a different shape, so that the table can be easily retrofitted for the particular surgery to be performed.

The cushion is pumped up by the introduction of a fluid (for instance, a gas such air), under pressure into the cushion until the patient is brought into the desired position. If, in the course of the treatment, a flat patient position is required again, the pressure of the cushion filling is reduced in staged doses until the desired new patient position has been attained. Control of the cushion pressure can occur via a foot switch with which the treating surgeon can control all movements without using his hands. In this way, his hands can, for instance, remain sterile.

In another embodiment of the present invention, instead of a gas, a liquid can be employed to fill the cushion. This is an advantage if, for instance, acoustic waves (such as diagnostic and/or therapeutic ultrasonic, pressure or shock waves) are used.

It is advantageous if the liquid (e.g., water) is acoustically matched to the patient's body. "Coupling cushions" of this type are known, for instance, in extracorporal lithotrity. In this event, they are primarily employed to couple a therapy source to the already positioned patient, however, and not to attain movement of the patient.

In coupling cushions, as they are employed in lithotrity, complicated control of the cushion pressure ensures that as far as possible the patient does not move. In contrast to this, the goal of the current device is to bring the patient into the proper position via a suitable selection of cushion pressure.

Of course, acoustic waves can be coupled into the body via the current cushion in the same manner as employed by a known coupling cushion used in lithotrity.

Compared to the known devices which permit similar patient movements, this present invention described here offers a number of advantages:

The concept is especially economical, because it is relatively uncomplicated technologically.

The cushion can be easily used with currently existing tables, without needing to carry out comprehensive alterations.

The present invention is technically safe. In particular, the maximum pressure in the cushion can be limited via a safety valve or the like. Contrary to conventional adjustable surgical tables, with proper placement of the cushions, the problem of mechanical bruising is practically nonexistent.

The cushions can easily be designed in such a manner that, for instance, X-ray beams and other diagnostic and therapeutic means are unimpeded or are impeded only insignificantly.

A special advantage arises in the case of Trendelenburg tilting in urology. In this case, the legs of the supine patient are supported by means of leg retainers. Stretching the ureter is usually attained by tilting the patient table (including the leg retainers) 15° into a head-down position. Contrary to the known procedures, with the current arrangement only the patient's hip region is raised (without also moving the leg retainers). In relation to the horizontal initial position of the patient, the patient's supported knees remain on the same level. The angle between the patient's body and thigh is extended by this means. In conjunction with raising the hip region, the kidneys can shift further (in the direction of the head) than would be the case of head-down positioning with a constant angle between the body and the thighs. Stretching the ureter is improved thereby, which again facilitates introducing instruments into the ureter.

Other objects, advantages and novel features of the present invention will become apparent from the following detailed description of the invention when considered in conjunction with the accompanying drawings.

DETAILED DESCRIPTION OF THE DRAWINGS

Figure 1:
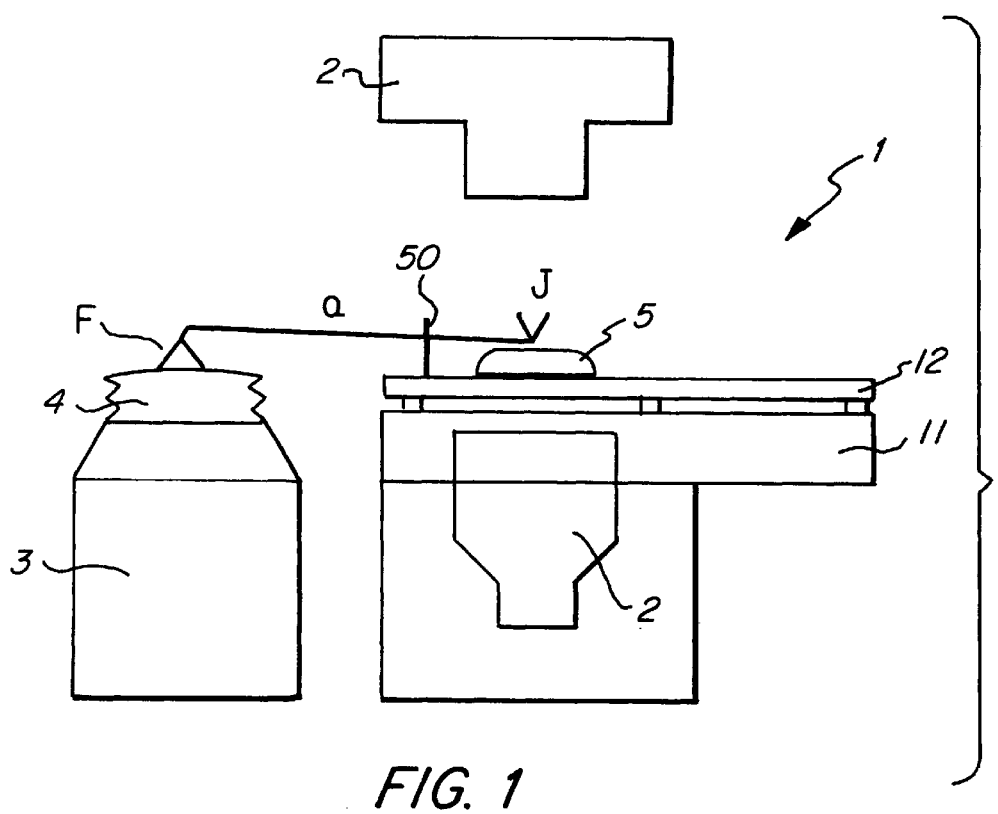
FIG. 1 is a first preferred embodiment of the present invention.

FIG. 1 shows a first preferred embodiment of the present invention in which the patient positioning table 1 itself is configured in a known manner, such as disclosed, for example, in European patent document EP 0 365 981 B1, and comprises both the actual support structure 11 and a table top 12. Either of these patient table and cot can be provided with leg retainers 50. The patient table 11 in conjunction with the table top 12 can be adjusted in such a manner that the to-be-crushed concretion is conveyed to a predetermined adjustment center J under observation with an X-ray locating device 2. Thereupon, the table top 12 is moved relative to the support structure 11 by the known distance a between the adjustment center J and the focus F of a therapy unit 3 (see FIG. 1), in such a manner that the concretion which is to be crushed is located in the focus F of the therapy unit 3. In order to be able to crush the stone or concretion, the table top 12 is provided with a window (not shown) which can be closed with a foil. A coupling cushion 4 of the therapy unit 3 is disposed close to the foil in such a manner that the impinging ultrasonic waves are practically not reflected at the interface. Any therapy units (particularly lithotrites) can be employed as the therapy unit 3 and as coupling cushion 4. The therapy unit and coupling cushion 4 are of conventional design, such as is disclosed, for example, in European patent document EP-A 369 177 and the state of the art mentioned therein and in the Search Report.

Moving out of the adjustment center of a locating device into the focus of a therapy device is one of the uses of the so-called floating table function. However, patient tables with floating table functions usually cannot be tilted, so they cannot be retrofitted for so-called Trendlelenburg tilting of the patient.

Therefore, according to the invention the table top 12 has at least one inflatable cushion 5 disposed thereon, by means of which the position of the patient (not depicted), or certain regions of the patient's body can be altered. In particular, the patient can be conveyed into a position corresponding to the Trendelenburg position. Depending on the surgical procedure to be carried out, the cushion 5 can be placed anywhere on the surgery table. In particular, the cushion can also be placed in the region through which (during lithotrity treatment, for example), therapy waves can be irradiated through the foil or through the window of the table top 12 into the patient's body.

Cushion 5 is filled with an ultrasound-permeable fluid and serves as an additional coupling medium so that the therapeutic ultrasonic waves from the therapy device 3 enter via coupling cushion 4 first into the cushion 5, and from this cushion into the patient's body. The fluid or liquid is matched to the properties of human tissue with regard to the acoustic impedance and the refraction index of the acoustic waves. By varying the filling of cushion 5, the human body can be selectively raised or lowered in the region where it lies on the cushion.

The supply pump, drain valve or vacuum pump, tubes and control means of the pump and drain valve are of conventional design, and therefore are not depicted in greater detail in the figures. Furthermore, if need be, the coupling cushion 4 and the cushion 5 may be designed as one unit.

Figure 2:
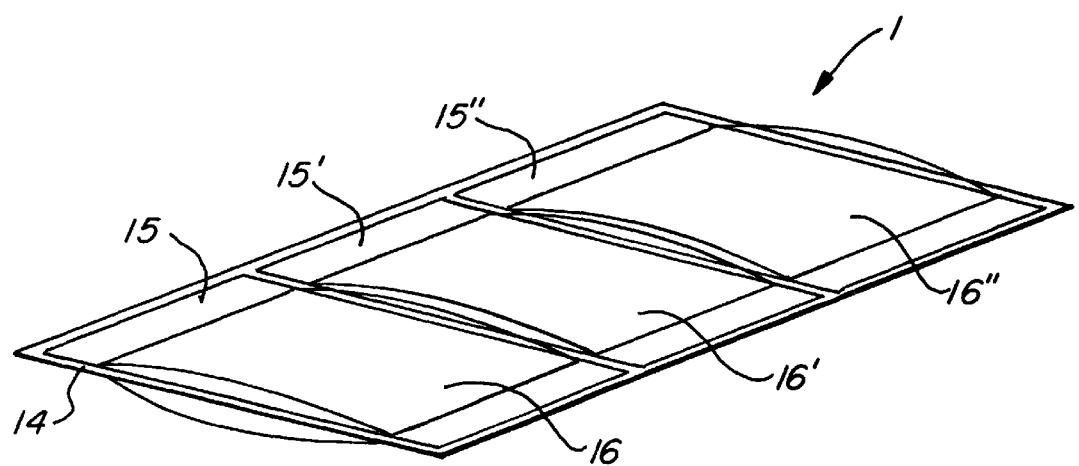
FIG. 2 is a second preferred embodiment of the present invention.

FIG. 2 shows another preferred embodiment of the present invention in which table 1 is designed approximately as in German patent document DE 38 28 087 C2. Table 1 is provided with a frame 14 to which a carrier foil is attached on which the patient can lie. The carrier foil of the illustrated preferred embodiment comprises three sections 15, 15' and 15". Integrated into each section is a cushion 16, 16' and 16", which can be inflated and deflated in a controlled manner by controlling the fluid filling via a control unit (not shown). Each section can be operated by a foot switch (also not depicted), in such a manner that the position of the patient lying on the cushion can be selectively and regionally adjusted.

The foil is preferably replaceable. This is advantageous not only for hygienic reasons, but it also permits the attachment of (to frame 14) foils of different shapes that are provided with cushions with shapes that can be matched to the respective conditions of use.

Figure 3:
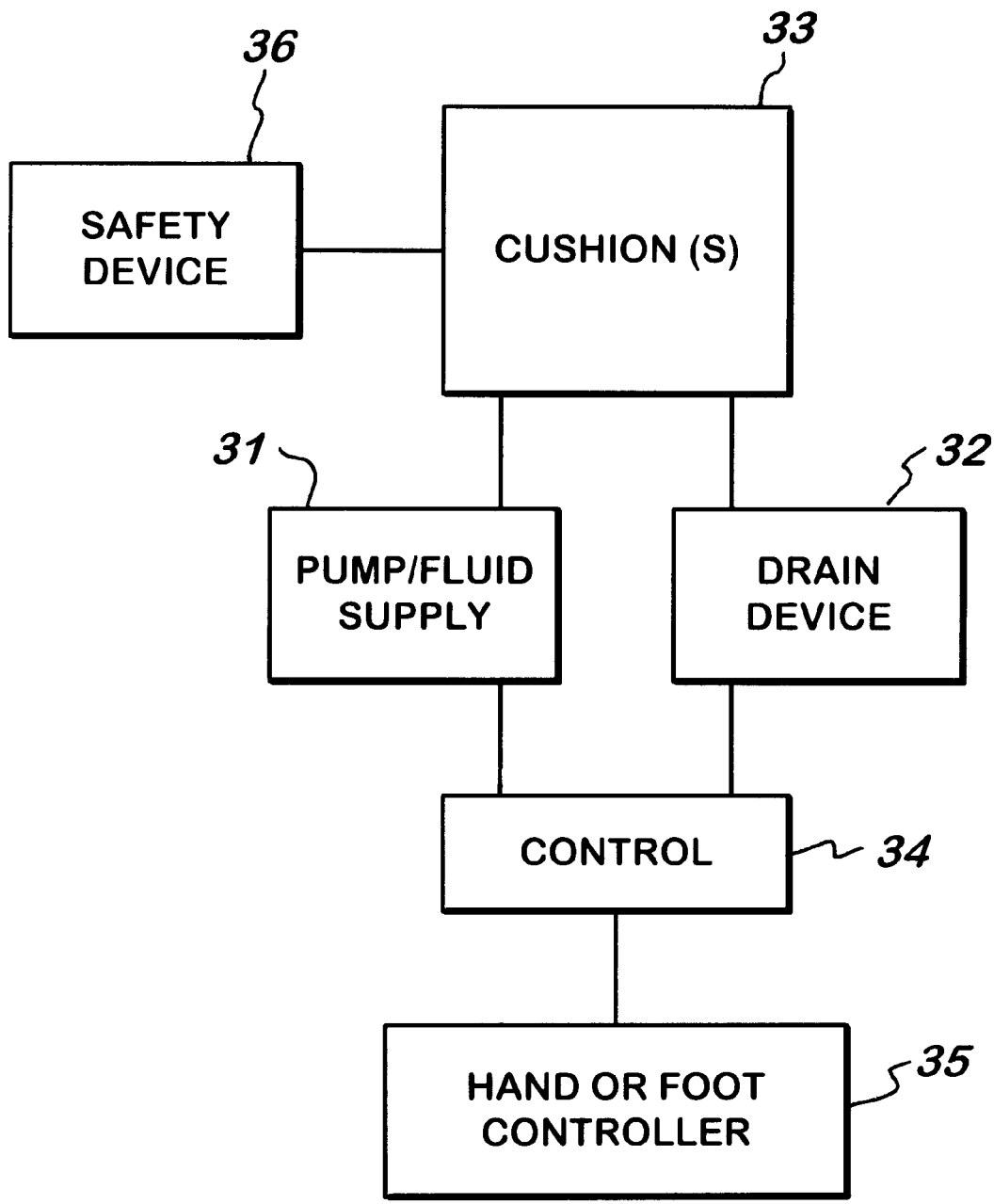
FIG. 3 is a schematic block diagram of a control arrangement for the positioning device according to the invention.

FIG. 3 illustrates a control arrangement for the positioning device according to the invention. A pump/fluid supply 31 and drain device 32 is connected to the cushion(s) 33 and supplies fluid and provides drainage thereof. A control device 34 that has an optional hand or foot control device 35 is connected to the pump/fluid supply 31 and drain device 32 and controls the filling and draining of the cushion(s) 33. Connected to the cushion(s) 33 is a safety device 36 which limits the maximum pressure of the cushion(s) 33.

In the preceding, the present invention is described using preferred embodiments. Of course, within the overall scope of the present invention a variety of modifications are possible:

Thus, in particular, if no ultrasonic treatment is to be performed in the region of the support surface on the cushion, the cushion can be filled with a gas so that the cushion is transparent for X-ray beams. In any event, with the present invention special positioning requirements demanded by medical examinations and therapeutic measures can be met in a simply, safe and economical manner.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A system for positioning a patient in a Trendelenburg head-down position during diagnostic and therapeutic analysis, comprising:
    a horizontally disposed bearer element for the patient;
    leg retainers positioned on the bearer element and extending upwardly therefrom to terminating at a level above the bearer element so as to support the knees of the patient at the level while the patient is supine to achieve a first angle between the patient's upper body and thighs; and
    an inflatable wedge-shaped cushion disposed along the bearer element and positioned for raising only the patient's hip region as the knees remain at the level so as to achieve a second angle between the upper body and thighs without displacing the leg retainers.

2. The system according to claim 1, wherein said inflatable cushion is inflatable and deflatable in a controlled manner using a gas.

3. The system according to claim 1, further comprising a liquid delivered to said inflatable cushion and a pump supplying the liquid, so that the liquid can be pumped up and drained in a controllable manner.

4. The system according to claim 3, wherein said liquid is permeable to acoustic waves.

5. The system according to claim 3, wherein said liquid is permeable to ultrasonic, pressure or shock waves.

6. The system according to claim 3, further comprising a cushion for coupling an ultrasonic source to the patient for at least one of therapeutic and diagnostic uses.

7. The system according to claim 1, further comprising a foot or hand controller for controlling a height of said cushion.

8. The system according to claim 1, further comprising a safety device which limits a maximum pressure of said cushion.

9. The system according to claim 1, wherein said wedge-shaped cushion is transparent to allow the passage of x-ray beams therethrough.

10. The system according to claim 1, wherein said cushion has a shape adapted to a respective condition of use.

11. The system according to claim 1, further comprising a control unit for regulating a supply pump and a drain device connected to said cushion.

12. The system according to claim 11, wherein said drain device is selected from the group consisting of a drain valve and a vacuum pump.

13. A system for positioning a patient in a Trendelenburg head-down position during a diagnostic and therapeutic analysis, comprising:
    a horizontally disposed elongated bearer element for horizontally supporting a body of the patient extending along an axis;
    leg retainers positioned on the bearer element to support the knees of the patient at a level above the bearer element while the patient is supine to achieve a first angle between the patient's upper body and thighs; and
    multiple inflatable cushions disposed side by side along the axis of the bearer element, said cushions being inflatable to varying degrees for raising only a hip region of the patient at a second angle between the upper body and thighs without displacing the leg retainers, so as to maintain the level at which the knees are supported unchanged as the hip region of the patient is displaced.

14. The system according to claim 13, wherein each of said inflatable cushions can be individually controlled.

15. The system according to claim 13, wherein:
    said inflatable cushions are replaceable and have different shapes.

16. The system according to claim 13, wherein said bearer element comprises a frame to which a carrier foil is attached and said cushions are integrated into said carrier foil.

* * * * *